(12) United States Patent
Kariathungal et al.

(10) Patent No.: US 8,179,396 B2
(45) Date of Patent: May 15, 2012

(54) SYSTEM AND METHODS FOR RULE-BASED VOLUME RENDITION AND NAVIGATION

(75) Inventors: Murali Kumaran Kariathungal, Hoffman Estates, IL (US); Mark Ricard, Naperville, IL (US)

(73) Assignee: General Electric Company, Schenectady, NY (US)

( * ) Notice: Subject to any disclaimer, the term of this patent is extended or adjusted under 35 U.S.C. 154(b) by 422 days.

(21) Appl. No.: 11/497,611

(22) Filed: Aug. 2, 2006

(65) Prior Publication Data

US 2008/0030501 A1 Feb. 7, 2008

(51) Int. Cl.
*G06T 13/00* (2011.01)
*A61B 5/05* (2006.01)
*A61B 8/00* (2006.01)

(52) U.S. Cl. .................. 345/474; 600/410; 600/437

(58) Field of Classification Search .................. None
See application file for complete search history.

(56) References Cited

U.S. PATENT DOCUMENTS

| | | | | |
|---|---|---|---|---|
| 5,630,421 A * | 5/1997 | Barlow et al. | ............ | 600/459 |
| 5,872,575 A * | 2/1999 | Segal | ............ | 345/473 |
| 6,266,387 B1 * | 7/2001 | Gscheidmeier et al. | ............ | 378/4 |
| 6,331,861 B1 * | 12/2001 | Gever et al. | ............ | 345/629 |
| 6,482,161 B1 * | 11/2002 | Sumanaweera et al. | ............ | 600/454 |
| 6,621,918 B1 * | 9/2003 | Hu et al. | ............ | 382/128 |
| 6,690,961 B1 * | 2/2004 | Kaufman et al. | ............ | 600/410 |
| 6,707,469 B1 | 3/2004 | Kelly | | |
| 7,248,260 B2 * | 7/2007 | Yamaguchi | ............ | 345/426 |
| 2002/0113794 A1 * | 8/2002 | Wu | ............ | 345/474 |
| 2002/0198447 A1 * | 12/2002 | Van Muiswinkel et al. | .. | 600/410 |
| 2003/0185426 A1 * | 10/2003 | Ohishi | ............ | 382/128 |
| 2004/0027359 A1 * | 2/2004 | Aharon et al. | ............ | 345/619 |

(Continued)

FOREIGN PATENT DOCUMENTS

WO 03100542 A2 12/2003

(Continued)

OTHER PUBLICATIONS

GE Healthcare, "Centricity AW Suite 2.0, Service Release Notes," Release 2.0 2032752-001 Rev 1, Published Oct. 18, 2006; 33 pages.

(Continued)

*Primary Examiner* — Joni Hsu
*Assistant Examiner* — David H Chu
(74) *Attorney, Agent, or Firm* — McAndrews, Held & Malloy, Ltd.; Armando Pastrana, Jr.

(57) ABSTRACT

Certain embodiments of the present invention provide a method for clinical presentation of a radiological study including: associating a customizable set of rules with image data corresponding to at least a portion of the radiological study; and rendering automatically the image data to form volumetric data; and navigating automatically the volumetric data with the customizable set of rules to present a navigated the at least a portion of the radiological study to a user. In an embodiment, the system further includes halting the navigating automatically the volumetric data from an interaction by the user. In an embodiment, the rendering automatically the image data is initiated from an interaction by the user. In an embodiment, the navigating automatically the volumetric data is initiated from an interaction by the user. In an embodiment, both the rendering automatically the image data and the navigating automatically the volumetric data are initiated an interaction by the user. In an embodiment, the customizable set of rules includes at least one of: a rendering rule and a navigation rule.

21 Claims, 4 Drawing Sheets

U.S. PATENT DOCUMENTS

| | | | |
|---|---|---|---|
| 2005/0021377 A1* | 1/2005 | Dobbs et al. | 705/3 |
| 2005/0063575 A1* | 3/2005 | Ma et al. | 382/128 |
| 2005/0096539 A1* | 5/2005 | Leibig et al. | 600/437 |
| 2005/0107695 A1* | 5/2005 | Kiraly et al. | 600/431 |
| 2006/0025674 A1* | 2/2006 | Kiraly et al. | 600/410 |
| 2006/0111937 A1 | 5/2006 | Yarger et al. | |
| 2006/0114254 A1* | 6/2006 | Day et al. | 345/424 |
| 2006/0132482 A1* | 6/2006 | Oh | 345/419 |
| 2007/0032720 A1* | 2/2007 | Koivukangas et al. | 600/407 |
| 2007/0103459 A1* | 5/2007 | Stoval et al. | 345/419 |
| 2007/0106633 A1* | 5/2007 | Reiner | 707/1 |
| 2007/0188501 A1* | 8/2007 | Yee et al. | 345/473 |
| 2007/0238948 A1* | 10/2007 | Bartsch et al. | 600/407 |
| 2008/0140722 A1* | 6/2008 | Jakobovits | 707/104.1 |
| 2008/0232661 A1* | 9/2008 | Habets et al. | 382/128 |
| 2008/0273775 A1* | 11/2008 | Hilbelink | 382/128 |

FOREIGN PATENT DOCUMENTS

| | | |
|---|---|---|
| WO | 2005008591 A2 | 1/2005 |
| WO | 2005051197 A2 | 6/2005 |

OTHER PUBLICATIONS

GE Healthcare, "Centricity AW Suite 2.0, Customer Release Notes," Release 2.0 2032753-001 Rev 1, Published Oct. 18, 2006; 25 pages.
International Search Report, EP 07 11 3294, dated Oct. 14, 2011.
Konrad Muehler, Ragnar Bade and Bernhard Preim: "Adaptive script based animations for medical education and intervention planning", Technical Report (Otto-Von-Guericke Universitat Magdeburg), Feb. 17, 2006; XP002662758.
European Patent Office Communication; Application No. 07113294; European Search Report; (7 pages) Nov. 16, 2011.

\* cited by examiner

| Rule Number | Rule Description |
|---|---|
| 1 | Pan volume to the left by a predefined amount |
| 2 | Rotate volume counterclockwise by a predefined amount |
| 3 | Zoom into volume by a predefined amount |
| 4 | Apply a predefined lookup table corresponding anatomy in the volume |
| 5 | Adjust brightness and contrast by a predefined amount |

304

| Rule Number | Rule Description |
|---|---|
| 1 | Zoom into the volume by a predefined amount |
| 2 | Rotate the volume by a predefined amount |
| 3 | Show a two dimensional oblique plane of the volume |
| 4 | Synchronize two-dimensional views of the volume |
| 5 | Apply a brightness by a predefined amount to the volume |
| 6 | Rotate the volume by a predefined amount |
| 7 | Apply a predefined lookup table corresponding to lung tissue |

306

| Rule Number | Rule Description |
|---|---|
| 1 | Perform Maximum Intensity Projection for rendering |
| 2 | rotation duration=1 sec |
| 3 | zoom zoomfactor=2.0 |
| 4 | applylut lut=LUNG |
| 5 | windowlevel window=1000.0 level=500.0 |

FIG. 4

Example Rule in XML

```
<Volume Navigation>
    <Rules>
        <Rule name=rule1 default=yes>
            <Render type>Maximum Intensity Projection</Render type>
            <Operation type=rotation duration=1 sec/>
            <Operation type=zoom zoomfactor=2.0/>
            <Operation type=applylut lut=LUNG/>
            <Operation type=windowlevel window=1000.0 level=500.0/>
        </Rule>
    </Rules>
</Volume Navigation>
```

400

SYSTEM AND METHODS FOR RULE-BASED VOLUME RENDITION AND NAVIGATION

BACKGROUND OF THE INVENTION

Embodiments of the present application relate generally to rule-based volume generation and navigation. Particularly, certain embodiments relate to automatic rule-based volume generation and navigation for picture archiving and communications systems ("PACS").

Diagnostic Workstations, such as PACS workstations and Advantage Workstation®, have become an increasingly helpful tool for radiologists and other clinicians who work with radiological images. For example, a radiologist is able to use a computer workstation running one or more clinical applications (PACS Workstation, Advantage Workstation, etc.) to read a patient's study. The workstation may allow the clinician (e.g. a radiologist, cardiologist, technician, etc.) to view radiological image data in a variety of dimensions, orientations, colors, hues, shades, sizes, rotations, and/or the like.

A computer workstation may allow a user, such as a clinician, to interact with an application. An application may include features for viewing a radiological image and/or study. For example, an application may have a view port through which one or more radiological images are viewable. A number of user interactions may generally be required for a clinician, such as a radiologist, to obtain a view of a patient's study and/or image that will be useful for clinical purposes. For example, upon loading a CT study, a user may direct the rendering of a volumetric image through an application employing reconstruction algorithms. Such user direction may involve multiple mouse clicks, or multiple uses of a mousing device. Furthermore, once the image has been rendered, a user may navigate the image using multiple mousing interactions, such as mouse clicks, mouse drags, and/or the like.

A radiological imaging device, such as computed tomography ("CT") or magnetic resonance ("MR"), may generate and acquire one or more radiological images. An acquired image may include a series of two-dimensional images. The two-dimensional images may be reconstructed or rendered to form a higher dimensional image, such as a three-dimensional image or a four-dimensional image (e.g. three-dimensional image shown over time).

Certain applications may enable a user to interact and direct volume rendering in the following manner. First a user may launch a volume rendering application through an action, such as selecting, clicking, actuating, and/or the like. Next the user may select the study for volume rendering. After these steps, the application may then render the volume, for example, with a default volume rendering protocol.

In an integrated environment with PACS, volume rendering may involve the following steps. First, a user selects a study for reading, for example, using a PACS workstation. If the study contains multiple series, the user may be further required to select the series he wants to load in the volume rendering application. Next, the user must start the volume rendering application. This may be done, for example, by selecting a volume rendering protocol. Next, the user must initiate volume rendering in the application. After this, the volume may be constructed in the volume rendering application.

After rendering or reconstruction, it may be helpful to further navigate or further process the rendered or reconstructed image. Every desired navigational result may potentially require multiple user interactions. For example, to rotate the volume, a user may select a "rotate" tool. Selection of the tool may be accomplished, for example by right clicking and selecting the tool or by selecting the tool from a tool palette, and dragging a mousing device in the direction of the desired rotation on the display, for example. As another example, to zoom the image, a user may select the "zoom" tool and drag the mouse to zoom in or zoom out on the displayed image, for example. As another example, to change window level parameters (e.g., contrast and brightness), a user may select a "window/level" tool and drag the mousing device on the display, for example. To perform a combination of such functions (e.g. rotate, window/level, etc.) may involve numerous interactions. However, repetitive use of a mousing device or other interface device may not be preferable.

Furthermore, the behavior of many clinicians when reading a radiological study may be somewhat repetitive and/or predictable. For example, a radiologist may have his/her own characteristic way for navigating a volume. A radiologist, for example, may also have a variety of different techniques that he or she employs during image analysis.

Thus, there is a need for methods and systems that reduce the number of user interactions when rendering and/or navigating a volume. Additionally, there is a need for methods and systems that allow a user to easily deviate from any automated program for reducing interactions. There is a need for methods and systems that facilitate consistent results when rendering and navigating a radiological study.

BRIEF SUMMARY OF THE INVENTION

Certain embodiments of the present invention provide a method for clinical presentation of a radiological study including: associating a customizable set of rules with image data corresponding to at least a portion of the radiological study; and rendering automatically the image data to form volumetric data; and navigating automatically the volumetric data with the customizable set of rules to present a navigated the at least a portion of the radiological study to a user. In an embodiment, the system further includes halting the navigating automatically the volumetric data from an interaction by the user. In an embodiment, the rendering automatically the image data is initiated from an interaction by the user. In an embodiment, the navigating automatically the volumetric data is initiated from an interaction by the user. In an embodiment, both the rendering automatically the image data and the navigating automatically the volumetric data are initiated an interaction by the user. In an embodiment, the customizable set of rules includes at least one of: a rendering rule and a navigation rule. In an embodiment, the customizable set of rules are customizable based on at least one of: a modality that generated at least a portion of the radiological study; an anatomy of a patient in at least a portion of the radiological study; an identity of the user; a preference of the user; and a procedure performed on the patient in at least a portion of the radiological study. In an embodiment, the rendering and the navigating are performable by a PACS workstation. In an embodiment, a plurality of customizable sets of rules are associated with at least a portion of the radiological study. In an embodiment, a customizable set of rules is selected from the plurality of customizable sets of rules based in part on at least one of: a modality that generated of at least a portion of the radiological study; an anatomy of a patient in at least a portion of the radiological study; an identity of the user; a preference of the user; a default status of one of the plurality of the set of rules; a priority status of one of the plurality of the set of rules; and a procedure performed on the patient in at least a portion of the radiological study.

Certain embodiments of the present invention provide a system for clinical presentation of a radiological study including: a user interface for of receiving a user interaction; a communications link for receiving image data corresponding to at least a portion of the radiological study; and a processor capable of rendition of the image data to form volumetric data, and navigation of the volumetric data, wherein the processor automatically performs the navigation of the volumetric data upon the user interaction using a customizable set of rules. In an embodiment, the processor halts the navigation upon a subsequent user interaction. In an embodiment, the processor automatically performs the rendition upon the user interaction. In an embodiment, the processor forms a part of a PACS workstation. In an embodiment, the customizable set of rules includes at least one of: a rendering rule and a navigation rule. In an embodiment, the customizable set of rules are customizable based on at least one of: a modality that generated at least a portion of the radiological study; an anatomy of a patient in at least a portion of the radiological study; an identity of the user; a preference of the user; and a procedure performed on the patient in at least a portion of the radiological study. In an embodiment, a plurality of customizable sets of rules is associated with at least a portion of the radiological study. In an embodiment, a customizable set of rules is selected from the plurality of customizable sets of rules based in part on at least one of: a modality that generated at least a portion of the radiological study; an anatomy of a patient in at least a portion of the radiological study; an identity of the user; a preference of the user; a default status of one of the plurality of the set of rules; a priority status of one of the plurality of the set of rules; and a procedure performed on the patient in at least a portion of the radiological study.

Certain embodiments of the present invention provide a computer-readable storage medium including a set of instructions for a computer, the set of instructions including: a rendering routine for rendering image data associated with a radiological study into volumetric data; and a navigation routine for navigating automatically the volumetric data based on a customizable set of rules associated with the radiological study. In an embodiment, the navigation routine is performed automatically upon a user interaction. In an embodiment, the customizable set of rules includes at least one of: rendering rule and a navigation rule. In an embodiment, the customizable set of rules are customizable based on at least one of: a modality that generated at least a portion of the radiological study; an anatomy of a patient in at least a portion of the radiological study; an identity of the user; a preference of the user; and a procedure performed on the patient in at least a portion of the radiological study. In an embodiment, a plurality of customizable sets of rules is associated with at least a portion of the radiological study. In an embodiment, a customizable set of rules is selected from the plurality of customizable sets of rules based in part on at least one of: a modality that generated at least a portion of the radiological study; an anatomy of a patient in at least a portion of the radiological study; an identity of the user; a preference of the user; a default status of one of the plurality of the set of rules; a priority status of one of the plurality of the set of rules; and a procedure performed on the patient in at least a portion of the radiological study. In an embodiment, the navigation routine is capable of halting upon a user interaction. In an embodiment, the set of instructions further includes an association routine for associating the set of rules with the image data.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings. Further, some figures may be representations of the type of display and/or output associated with methods and systems of the present invention, in accordance with one or more embodiments.

DETAILED DESCRIPTION OF THE INVENTION

Figure 1:
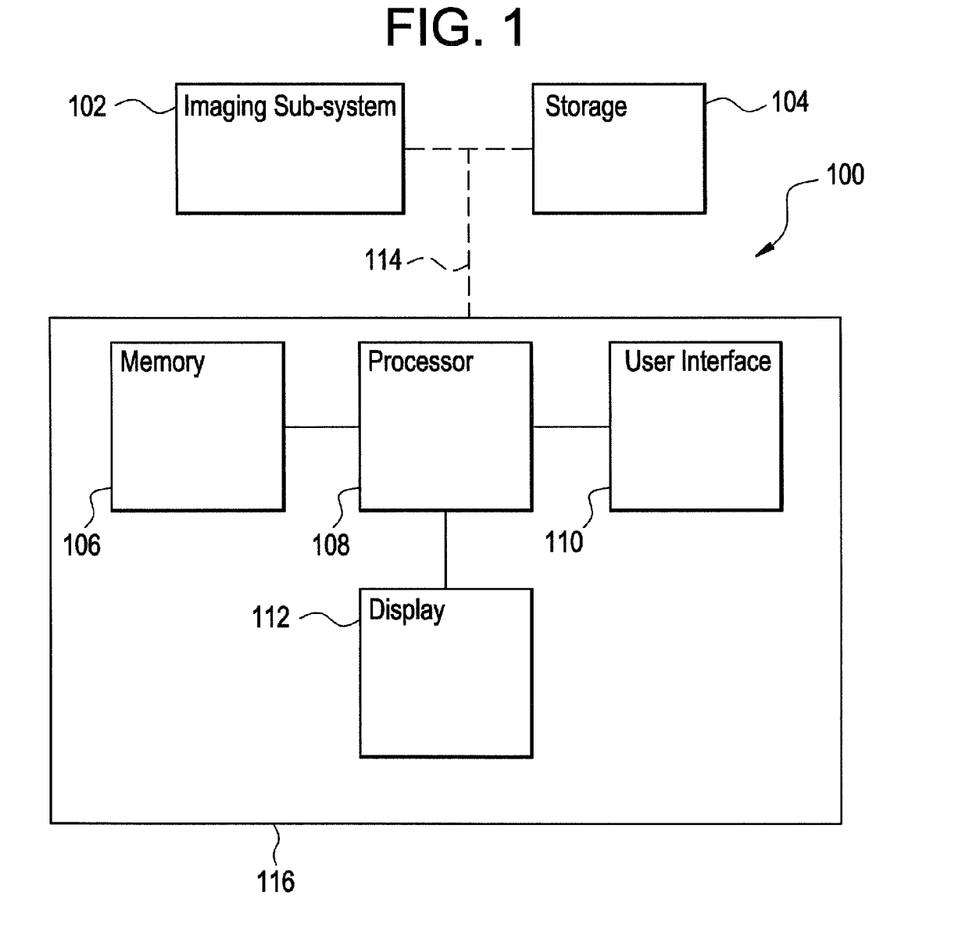
FIG. 1 shows a system for clinical presentation of a radiological study, in accordance with an embodiment of the present invention.

FIG. 1 shows a system 100 for clinical presentation of a radiological study, in accordance with an embodiment of the present invention. A system 100 may include an imaging subsystem 102 communicatively linked to a processing subsystem 116, tracking subsystem 118, and/or a storage 104 through one or more communications links 114.

An imaging subsystem 102 may be any radiological system capable of generating two-dimensional, three-dimensional, and/or four-dimensional data corresponding to a volume of interest of a patient, potentially including foreign objects therein. Some types of image processing subsystems 102 include computed tomography (CT), magnetic resonance imaging (MRI), x-ray, positron emission tomography (PET), tomosynthesis, ultrasound, and/or the like, for example. An imaging subsystem 102 may include a fluoroscopic and/or angiographic system, for example. An imaging subsystem 102 may be capable of generating images of at least a portion of a volume of interest substantially in real-time, for example. An imaging subsystem 102 may generate one or more data sets including image data which may be communicated over a communications link 114 to a storage 104 and/or a processing subsystem 116.

A storage 104 may be capable of storing set(s) of data generated by the imaging subsystem 102 and/or tracking subsystem 118, for example. The storage 104 may be, for example, a digital storage, such as a PACS storage, an optical medium storage, a magnetic medium storage, a solid-state storage, a long-term storage, a short-term storage, and/or the like. A storage 104 may be integrated with imaging subsystem 102, and/or processing subsystem 116, for example. A storage 104 may be locally or remotely located, for example. A storage 104 may be persistent or transient, for example.

A processing subsystem 116 may further include a memory 106, a processor 108, a user interface, 110 and/or a display 112. The various components of the processing subsystem 116 may be communicatively linked. Some of the components may be integrated, such as, for example processor 108 and memory 106. The processing subsystem 116 may receive data corresponding to a volume of interest of a study from either an imaging subsystem 102, and/or storage 104, for example. The processing subsystem 116 may be communicatively linked to the imaging subsystem 102, and/or storage 104 through one or more communication links 114, for example. Communications between various components of system 100 may be continuous, intermittent, on-demand, and/or the like, for example. Data received by processing subsystem 116 may be stored in memory 106, for example. A processing subsystem 116 may be a PACS workstation, or a portion thereof, for example.

A memory 106 may be a computer-readable memory, for example, such as a hard disk, floppy disk, CD, CD-ROM, DVD, compact storage, flash memory, random access memory, read-only memory, electrically erasable and programmable read-only memory and/or other memory. A memory 106 may include more than one memory types for example. A memory 106 may be able to store data temporarily or permanently, for example. A memory 106 may be capable or storing a set of instructions readable by processor 108, for example. A memory 106 may also be capable of storing data generated by image generation subsystem 102, for example. A memory 106 may also be capable of storing data generated by processor 108, for example.

A processor 108 may be a central processing unit, a microprocessor, a microcontroller, and/or the like. A processor 108 may include more than one processors/processing units, for example. A processor 108 may be an integrated component, or may be distributed across various positions, for example. A processor 108 may be capable of executing an application, for example. A processor 108 may be capable of executing any of the methods in accordance with the present invention, for example. A processor 108 may be capable of receiving input information from a user interface 110, and generating output displayable by a display 112, for example.

A user interface 110 may include any device(s) capable of communicating information from a user to a processing subsystem 116, for example. A user interface 110 may include a mousing device (e.g. a mouse), keyboard, and/or any other device capable of receiving a user directive. For example a user interface 110 may include voice recognition, motion tracking, and/or eye tracking features, for example. A user interface 110 may be integrated into other components, such as display 112, for example. As an example, a user interface 110 may include a touch responsive display 112, for example. A user interface 110 may relay user interactions, such as mouse clicks, mouse drags, mousing device actuations, and key strokes to other components of the processing subsystem 116, for example.

A display 112 may be any device capable of communicating visual information to a user. For example, a display 112 may include a cathode ray tube, a liquid crystal diode display, a light emitting diode display, a projector and/or the like. A display 112 may be capable of displaying radiological images and data generated by processing subsystem 116, for example. A display may be two-dimensional, but may be capable of indicating three-dimensional information through shading, coloring, and/or the like.

Figure 2:
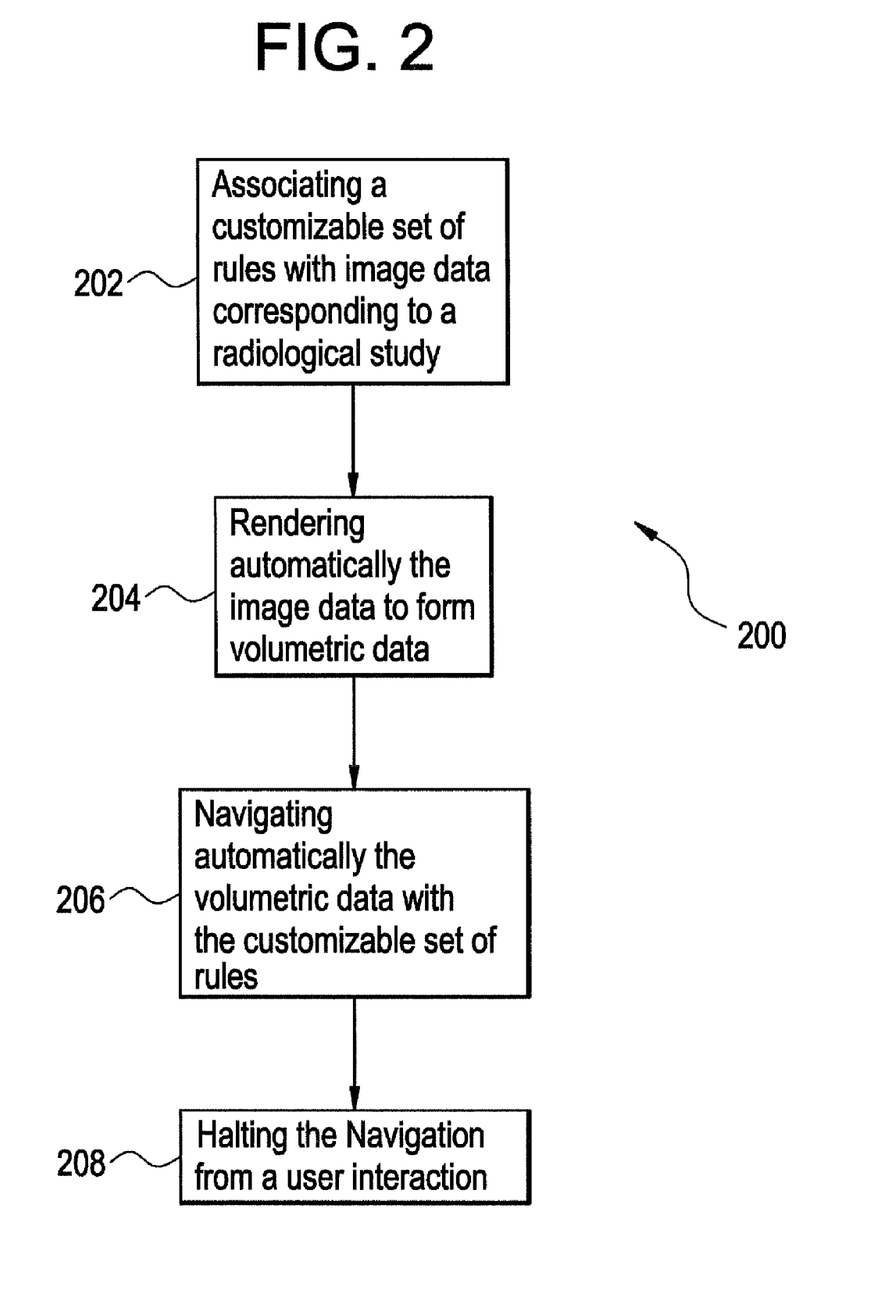
FIG. 2 shows a flow chart for a method for clinical presentation of a radiological study, in accordance with an embodiment of the present invention.

FIG. 2 shows a flow chart for a method 200 for clinical presentation of a radiological study, in accordance with an embodiment of the present invention. At least a portion of steps of method 200 may be performed in an alternate order and/or substantially/partially simultaneously, for example. Some steps of method 200 may also be omitted, for example, step 208. Method 200 may be performed, in part, by one or more processors, for example.

At step 202 customizable set of rules is associated with image data corresponding to a radiological study. A radiological study may have a variety of associated information.

For example, a radiological study may be generated by one or more procedures, and may have the corresponding information regarding the generating procedure(s). For example, a radiological study may contain information corresponding to the patient, the imaging modality (modalities), the anatomy (anatomies) imaged, the clinician performing the procedure, and/or the like.

Figure 3:
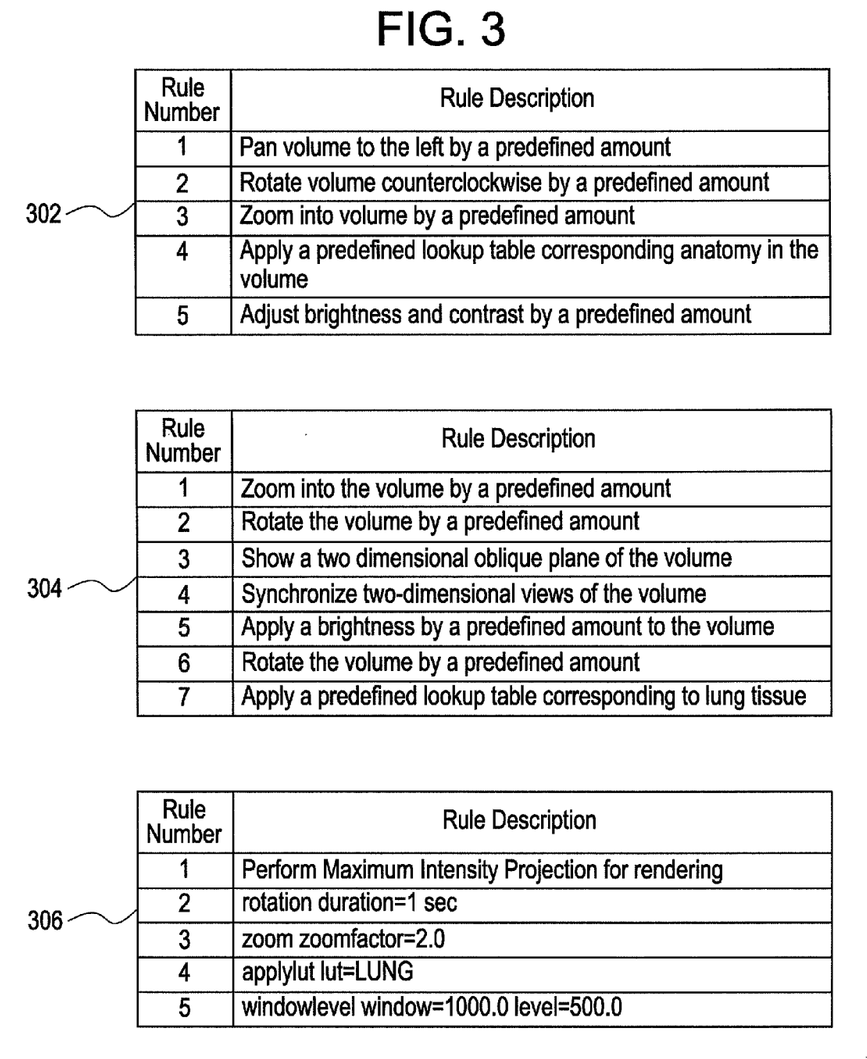
FIG. 3 shows customizable sets of rules, in accordance with an embodiment of the present invention.

It may be also possible to associate one or more configurable sets of rules with the radiological study. Turning for a moment to FIG. 3, various customizable sets of rules 302, 304, and 306, are shown, in accordance with an embodiment of the present invention. The sets of rules 302, 304, and 306 may each individually be customizable, for example. Rules may be added and/or removed from a set of rules. Rules may be customized according to clinician preference, clinical application, capabilities/limitations of the display/processor, and/or the like. Rules may be customized through interaction with navigation software (e.g. by navigating with a mouse through a study to develop a set of rules), or through other methods such as text entry in a spreadsheet-type interface, for example. Rules may be generated at the time of rendering/navigation based on various parameters (e.g. modality, clinician identity, clinician preference, anatomy, patient, procedure, etc.). Further, additional sets may be added/removed, for example.

Rules may instruct a processing subsystem (e.g. processing subsystem 116) how to perform automatic navigation (discussed below). Rules may also instruct a processing subsystem (e.g. processing subsystem 116) how to perform automatic rendering (discussed below). Thus, rules may be either for rendering and/or for navigation or for a combination thereof.

For example, a non-inclusive list of some types of navigation rules may include the following: window/level; rotating; zooming in/out; synchronizing views (e.g. 2D views within a particular volume, or 2D views across multiple volumes); applying a look-up table (LUT); panning; adjusting a brightness level; adjusting a contrast level; and selecting and viewing a particular two-dimensional plane (e.g. oblique, saggital, etc.). A look-up table (LUT) may be useful for converting pixel information to gray-scale values, or to other types of information (e.g. contrast, angulation, brightness, color, etc.). Each rule may have various parameters associated, for example (e.g. rotate by 45 degrees or for 3 seconds, zoom in by 150%, apply a LUT corresponding to lung tissue). Parameters may be constants or variables, for example. An example of a variable parameter would be a parameter corresponding to the anatomy imaged. So, if a study is for lung tissue, then the parameter corresponds to lung tissue. Alternatively, if a study is of an arm, the parameter corresponds to an arm. For example, various LUTs may be selected based on the anatomy imaged, and a variable parameter may assist to this end.

For example a non-inclusive list of some types of rendering rules may include the following: perform maximum intensity projection; perform minimum intensity projection; apply advanced algorithms such as vessel analysis, colon analysis, cardiac algorithms, etc.

Figure 4:
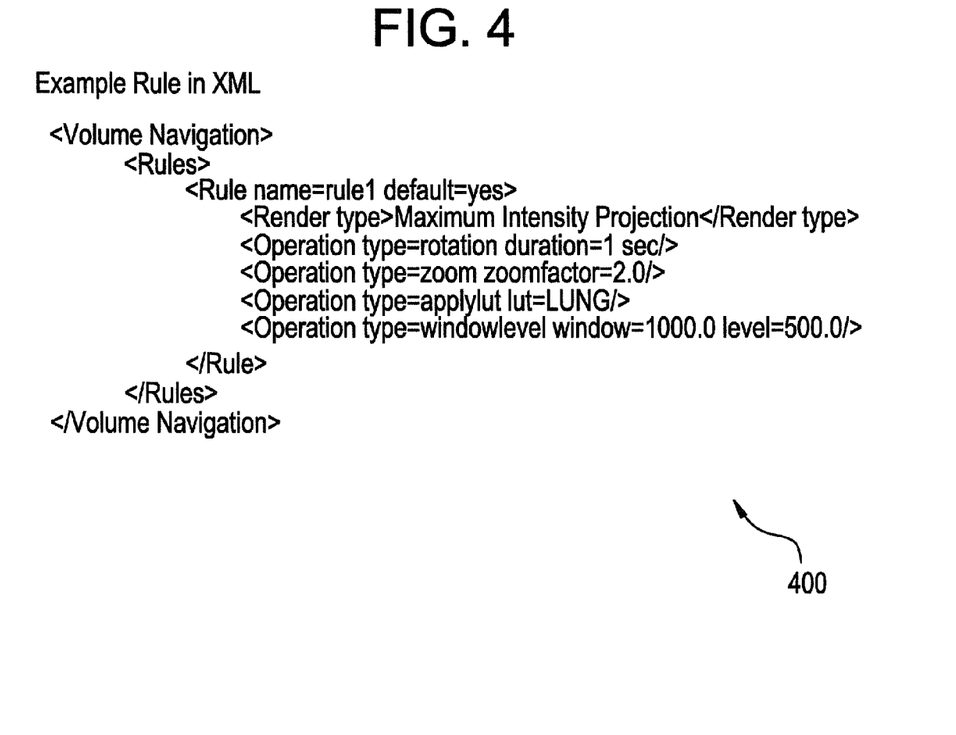
FIG. 4 shows a set of rules, in accordance with an embodiment of the present invention.

Turning for a moment to FIG. 4, a sample rule 400 is shown in accordance with an embodiment of the present invention. The particular rule is coded in XML, although a variety of other types of coding (e.g. textual, graphical) may be possible, for example. The sample rule 400 roughly corresponds to the set of rules 306 shown in FIG. 3. The set of rules contains the actual rules and also may contain some additional information (e.g. metadata). Such additional information may include, for example the name of the rule, the default status of the rule, the priority status of the rule, an association of the rule with a procedure, an association of the rule with a clinician, an association of the rule with a type of processing subsystem, and/or the like.

Set(s) of rules (302, 304, and/or 306) may be associated with a radiological study in a variety of manners. The association may be physical or logical, for example. The association may be performed a priori, or may occur at the time of image rendering/navigation. An association may be automatic, or may be manually performed, for example. The rules may form a part of the study, or a series thereof, for example. As another example, the rules may reside elsewhere (e.g. in a table stored in a memory). One or more software applications may be able to determine and associate a set of rules to be executed when processing a radiological study image data, for example.

Various different sets of rules may be available for association, for example. In this case, a software application may be able to select from one or more sets of rules based on particular criterion/criteria, for example. A non-inclusive list of potential selection criteria include the following: the modality that generated a radiological study (or series thereof); an anatomy of a patient in the radiological study; an identity of a clinician (e.g. user); a preference of a clinician; a default status of the sets of rules; a priority status of the sets of rules; and a procedure performed on the patient in the radiological study (or series thereof).

At step 204 the image data is automatically rendered to form volumetric data. Image data stored in a study (or a series thereof) may be two-dimensional. Rendering may take such two-dimensional data and create a three (our four) dimensional model in the form of volumetric data, for example. Image data may be rendered according to the associated set of rules from step 202, for example. Alternatively, image data may be rendered into volumetric data according to prescribed methods, for example. Volumetric data may be rendered according to clinical usefulness and/or clinician preference, for example. Rendering may be performed by a processing subsystem (e.g. subsystem 116), such as a PACS workstation, for example. Rendering may be performed on one or more processors, for example. Rendering may be performed by an application or multiple applications executed on one or more processors, for example. Automatic rendering may be initiated by a user (e.g. clinician) mouse click and/or other user interaction, for example.

The resulting volumetric data may be displayable to a user, such as a clinician, on a display, for example. The data may be displayed in two, three, and/or four dimensions, for example. The data may be displayed, for example, by an application having a view port. Volumetric data may include one or more anatomic images of a patient, for example. For example, multiple three-dimensional images may be rendered when, for example, there are multiple series in a radiological study. Multiple volumes may also be displayed to a user, for example.

At step 206 the volumetric data is automatically navigated (also known as traversed) with the customizable set of rules. Navigation may be performed automatically without any additional user interaction, or may be triggered by an additional user interaction (e.g. a second mouse click), for example. Real-time navigation results may be displayed to a user, or only the end result may be displayed, for example. Navigation may be performed by a processing subsystem (e.g. subsystem 116), such as a PACS workstation, for example. Navigation results may be displayed, for example, through one or more view ports to a user (e.g. clinician). Navigation may be performed on one or more processors, for example. Navigation may be performed by an application or multiple applications executed on one or more processors, for example. Navigation may be performed by the same application that performs rendering, or by a different application, for example. Automatic navigation may be initiated by a user (e.g. clinician, radiologist, cardiologist, etc.) mouse click and/or other user interaction, for example.

At step 208 the automatic navigation is halted from a user interaction. A user viewing navigation may wish to halt automatic navigation, and may do so, for example, with a mouse click. A user may be able to perform manual navigation (e.g. not automatic) after halting automatic navigation. A user may also be able to perform manual navigation while automatic navigation is being executed, for example. A user may also be able to resume automatic navigation upon a subsequent user interaction (e.g. a subsequent mouse click).

As an illustrative example, method 200 may be performed in the following manner. Prior to performing method 200, a clinician performs a CT-Scan on a patient's lung. The resulting study contains multiple sets of two-dimensional image data slices. At step 202 a customizable set of rules is associated the study of the patient's lung. In this particular example, the set of rules in FIG. 4 are associated with the study. The association is performed automatically in the following manner. A clinician wishes to view the study of the patient's lung. The clinician uses a PACS workstation running an application for reading the images. The application allows the clinician to select the study for viewing. The clinician selects the study from the PACS workstation and clicks a mouse to open study for reading (a double click on the study, clicking mouse on a "Display Images" button, etc.). The application is aware of the identity of the clinician. The application is also aware of the nature of the study. The clinician prefers to have the set of rules shown in FIG. 4 associated with CT-Scans of lung tissue. The application then automatically associates the set of rules 400 with the image data in the study.

At step 204 the image data in the study of the patient's lung is automatically rendered to form volumetric data. The image data is in two-dimensional slices, and rendering creates volumetric data containing information in three dimensions. In this particular example, maximum intensity projection rendering is used in accordance with the first rule in the set of rules 400. The rules are executed by a rule engine, which forms a part of the application running on the PACS workstation.

At step 206 the volumetric data is automatically navigated (also known as traversed) with the customizable set of rules. In this example, no further user interaction is necessary to initiate automatic navigation. The rules in set 400 are executed in the order shown. First, the volume is rotated for one second. Next, the display zooms into the volume by a factor of 2.0. Next, a look-up table is applied to the data, corresponding to lung tissue. Finally, the window/level values are set so that window=1000.0 and level=500.0.

At step 208 the automatic navigation is halted from a user interaction. Before the navigation is complete, the radiologist wishes to halt automatic navigation. To accomplish this, the radiologist clicks the mouse a second time. The rule engine halts execution of the set of rules 400. In this particular example, the radiologist wishes to zoom in more. After the zooming rule (i.e. zoom=2.0), the radiologist clicks the mouse a second time. The radiologist then interacts with the application to manually navigate the volumetric data. The radiologist zooms to a factor of 4.0. Satisfied with the zoom level, the radiologist then reactivates automatic navigation with another user interaction (e.g. a right mouse click and drop-down menu selection). The rule engine then continues with automatic navigation according to the set of rules 400.

Turning back to FIG. 1, in an embodiment, system 100 includes a computer-readable medium, such as a hard disk, floppy disk, CD, CD-ROM, DVD, compact storage, flash memory and/or other memory. The medium may be in the processing subsystem 116, and/or in a separate subsystem. The medium may include a set of instructions capable of execution by a computer or other processor. The rendering, associating, navigating, and halting functions described above may be implemented as instructions on the computer-readable medium. For example, the set of instructions may include an association routine that associates a set of rules with a radiological study (or a portion thereof). Additionally, the set of instructions may include a rendition routine that renders image data from a study into volumetric data. Additionally, the set of instructions may include a navigation routine that navigates the volumetric data for display to a user. In an embodiment, the set of instructions may include a halting routine for halting the execution of the set of rules upon a user interaction.

Thus, embodiments of the present application provide methods and systems that reduce the number of user interactions when rendering and/or navigating a volume. Additionally, embodiments of the present application provide methods and systems that allow a user to easily deviate from any automated program for reducing interactions. Moreover, embodiments of the present application provide methods and systems that facilitate consistent results when rendering and navigating a radiological study.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A method for clinical presentation of a radiological study, the method comprising:
  associating a pre-configured set of rendering and navigation rules with two-dimensional medical imaging data according to at least one of a radiological modality of the radiological study, a procedure of the radiological study, or an identity of a user;
  receiving a first single user interaction configured to initiate execution of the pre-configured set of rendering and navigation rules;
  executing, with a processing subsystem, the pre-configured set of rendering and navigation rules, wherein the pre-configured set of rendering and navigation rules is executed according to an execution order;
  rendering automatically the two-dimensional medical image data of at least a portion of the radiological study to form a three-dimensional model;
  navigating automatically the three-dimensional model according to the execution order to present a navigated radiological study; and
  halting said navigating automatically the three-dimensional model in response to a second single user interaction performed during navigation.

2. The method of claim 1, wherein the pre-configured set of rendering and navigation rules comprises at least two of rotating, zooming, synchronizing views, applying a look-up table, panning, adjusting a brightness level, adjusting a contrast level, or selecting a two-dimensional plane.

3. The method of claim 1, wherein the pre-configured set of rendering and navigation rules is selected from a plurality of pre-configured sets of rendering and navigation rules.

4. The method of claim 1, wherein said rendering automatically the two-dimensional medical image data is performed according to an order of the pre-configured set of rendering and navigation rules.

5. The method of claim 4, wherein the pre-configured set of rendering and navigation rules comprises at least two of a maximum intensity projection, a minimum intensity projection, a vessel analysis, a colon analysis, or a cardiac algorithm.

6. The method of claim 1, wherein the pre-configured set of rendering and navigation rules includes applying a lookup table according to an anatomy of the radiological study.

7. The method of claim 1, comprising customizing a set of rendering and navigation rules to form the pre-configured set of rendering and navigation rules.

8. A system for clinical presentation of a radiological study, the system comprising:
  a user interface configured to receive user interactions;
  a communications link configured to receive two-dimensional medical image data corresponding to the radiological study; and
  a processor configured to:
    associate a pre-configured set of rendering and navigation rules with the two-dimensional medical image data according to at least one of a radiological modality of the radiological study, a procedure of the radiological study, or an identify of a user;
    execute, in response to a first single user interaction received at the user interface, the pre-configured set of rendering and navigation rules according to an execution order;
    automatically render the two-dimensional medical image data of at least a portion of the radiological study to form a three-dimensional model;
    automatically navigate the three-dimensional model according to the execution order of the pre-configured set of rendering and navigation rules; and
    halt the automatic navigation in response to a second single user interaction performed during navigation.

9. The system of claim 8, wherein the pre-configured set of rendering and navigation rules comprises at least two of rotating, zooming, synchronizing views, applying a look-up table, panning, adjusting a brightness level, adjusting a contrast level, or selecting a two-dimensional plane.

10. The system of claim 8, wherein the pre-configured set of rendering and navigation rules is selected from a plurality of pre-configured sets of rendering and navigation rules.

11. The system of claim 8, wherein the processor is configured to render the two-dimensional image data according to an order of the pre-configured set of rendering and navigation rules.

12. The system of claim 11, wherein the pre-configured set of rendering and navigation rules comprises at least two of a maximum intensity projection, a minimum intensity projection, a vessel analysis, a colon analysis, or a cardiac algorithm.

13. The system of claim 8, wherein the pre-configured set of rendering and navigation rules includes applying a lookup table according to an anatomy of the radiological study.

14. The system of claim 8, wherein the processor is configured to customize a set of rendering and navigation rules to form the pre-configured set of rendering and navigation rules.

15. A non-transitory computer-readable storage medium including a set of instructions for a computer, the set of instructions comprising:
- an association routine for associating the pre-configured set of rendering and navigation rules with two-dimensional medical image data according to at least one of a radiological modality of the radiological study, a procedure of the radiological study, or an identity of a user;
- an execution routine for executing the pre-configured set of rendering and navigation rules in response to a first single user interaction, wherein the pre-configured set of rendering and navigation rules is executed according to an execution order;
- a rendering routine for rendering automatically the two-dimensional medical image data of at least a portion of the radiological study to form a three-dimensional model;
- a navigation routine for navigating automatically the three-dimensional model based on the execution order of the pre-configured set of rendering and navigation rules to present a navigated radiological study; and
- a halting routine for halting the navigation routine in response to a second single user interaction performed during navigation.

16. The non-transitory computer-readable medium of claim 15, wherein the pre-configured set of rendering and navigation rules comprises at least two of rotating, zooming, synchronizing views, applying a look-up table, panning, adjusting a brightness level, adjusting a contrast level, or selecting a two-dimensional plane.

17. The non-transitory computer-readable medium of claim 15, wherein the pre-configured set of rendering and navigation rules is selected from a plurality of pre-configured sets of rendering and navigation rules.

18. The non-transitory computer-readable medium of claim 15, wherein the rendering routine is configured to render the two-dimensional image data according to an order of the pre-configured set of rendering and navigation rules.

19. The non-transitory computer-readable medium of claim 18, wherein the pre-configured set of rendering and navigation rules comprises at least two of a maximum intensity projection, a minimum intensity projection, a vessel analysis, a colon analysis, or a cardiac algorithm.

20. The non-transitory computer-readable medium of claim 15, wherein the pre-configured set of rendering and navigation rules includes applying a lookup table according to an anatomy of the radiological study.

21. The non-transitory computer-readable medium of claim 15, comprising a customization routine for customizing a set of rendering and navigation rules to form the pre-configured set of rendering and navigation rules.

\* \* \* \* \*